United States Patent
Raval et al.

(10) Patent No.: US 12,396,964 B2
(45) Date of Patent: Aug. 26, 2025

(54) AMANTADINE HYDROCHLORIDE FOR THE TREATMENT OF TRAUMATIC BRAIN INJURY

(71) Applicants: Krunal Raval, Ahmedabad (IN);
Suresh Borsadia, Plainsboro, NJ (US);
Kalpana Patel, West Windsor, NJ (US);
Gurpartap Singh Sachdeva, Princeton Junction, NJ (US)

(72) Inventors: Krunal Raval, Ahmedabad (IN);
Suresh Borsadia, Plainsboro, NJ (US);
Kalpana Patel, West Windsor, NJ (US);
Gurpartap Singh Sachdeva, Princeton Junction, NJ (US)

(73) Assignee: Shinkei Therapeutics, Inc., Princeton, NJ (US)

( * ) Notice: Subject to any disclaimer, the term of this patent is extended or adjusted under 35 U.S.C. 154(b) by 0 days.

(21) Appl. No.: 18/049,892

(22) Filed: Oct. 26, 2022

(65) Prior Publication Data
US 2023/0082617 A1    Mar. 16, 2023

Related U.S. Application Data

(60) Provisional application No. 63/237,414, filed on Aug. 26, 2021.

(51) Int. Cl.
*A61K 31/13*    (2006.01)
*A61K 9/00*    (2006.01)
*A61K 9/08*    (2006.01)
*A61K 47/02*    (2006.01)

(52) U.S. Cl.
CPC ............ *A61K 31/13* (2013.01); *A61K 9/0019* (2013.01); *A61K 9/08* (2013.01); *A61K 47/02* (2013.01)

(58) Field of Classification Search
CPC ........ A61K 31/13; A61K 9/0019; A61K 9/08; A61K 31/04; A61K 47/02
See application file for complete search history.

(56) References Cited

U.S. PATENT DOCUMENTS

| | | | |
|---|---|---|---|
| 9,867,791 B2 * | 1/2018 | Went | A61P 25/00 |
| 11,707,439 B2 * | 7/2023 | Singh Sachdeva | A61K 9/0019 514/662 |
| 2020/0315991 A1 * | 10/2020 | Singh Sachdeva | A61K 9/0019 |

OTHER PUBLICATIONS

Severs et. al., (Jan. 23, 2014), A critical appraisal of intravenous fluids: from the physiological basis to clinical evidence, Nephrol Dial Transplant, 30, 178-187. (Year: 2014).*
Amin et. al., (Jun. 2006), In vitro Hemolysis Guidance for the Pharmaceutical Scientist, Journal of Pharmaceutical Sciences, 95, 1-4. (Year: 2006).*
Giacino et. al., (Mar. 1, 2012), Placebo-Controlled Trial of Amantadine for Severe Traumatic Brain Injury, N Engl J Med., 9, 819-826 (Year: 2012).*
Giacino et. al., (Mar. 1, 2012), Placebo-Controlled Trial of Amantadine for Severe Traumatic Brain Injury (Supplemental), N Engl J Med., 9, 1-71 (Year: 2012).*
Urso et. al., (2002), A Short introduction to pharmacokinetics, Euro. Rev. Med. Pharmacol. Sci., 6, 33-44 (Year: 2002).*
De Vries et. al., (Aug. 1, 2019), Bioavailability and Pharmacokinetics of Once-Daily Amantadine Extended-Release Tablets in Healthy Volunteers: Results from Three Randomized, Crossover, Open-Label, Phase 1 Studies, Neurol Ther, 8, 449-460 (Year: 2019).*
Urso et. al., (2002), A short introduction to pharmacokinetics, Eur. Rev. Med. Pharmacol. Sci., 6, 33-44. (Year: 2002).*
Brenner et. al., 1989, Amantadine sulphate in treating Parkinson's disease: Clinical effects, psychometric tests and serum concentrations, J Neurol, 236, 153-156 (Year: 1989).*
Giacino et. al., (Mar. 1, 2012), Placebo-Controlled Trial of Amantadine for Severe Traumatic Brain Injury, N Engl J Med., 9, 819-826 (including the Supplemental) (Year: 2012).*
Saniova et. al. (2004), The outcome of patients with severe head injuries treated with amantadine sulphate, J Neural Transm, 111, 511-514 (Year: 2004).*
Chambere, 2019, Principles of intravenous drug infusion, Pharmacology, 20, 61-64 (Year: 2019).*
Al-Adawi et.al. ((2009), Effect of amantadine on the sleep-wake cycle of an inpatient with brain injury, Brain Inj., 23, 559-650 (Year: 2009).*

* cited by examiner

*Primary Examiner* — Juliet C Switzer
*Assistant Examiner* — Dawanna Shar-Day White
(74) *Attorney, Agent, or Firm* — William D. Hare; McNeely, Hare & War, LLP

(57) ABSTRACT

The invention is a dosing regimen for administering an aqueous composition of amantadine hydrochloride to a patient having a traumatic brain injury. The dosing regimen includes administering a first dose and a second dose of amantadine hydrochloride by intravenous injection. The first dose comprises between 100-200 mg of amantadine hydrochloride in an aqueous solution of about 200-300 ml over a period of about two to about four hours. The second dose comprises between 100-200 mg of amantadine hydrochloride in an aqueous solution of about 200-300 ml over a period of about two to about four hours. The second dose is administered after about four to six hours after the first dose is fully administered.

21 Claims, No Drawings

AMANTADINE HYDROCHLORIDE FOR THE TREATMENT OF TRAUMATIC BRAIN INJURY

TECHNICAL FIELD OF THE INVENTION

The present invention provides a regime for the treatment of patients with traumatic brain injury (TBI) using intravenous amantadine hydrochloride. The regime disclosed in the present invention is helpful in treatment and recovery of the patients with TBI. The present invention also provides the dose and rate at which these doses should be provided to the patients.

BACKGROUND

The Centers for Disease Control and Prevention (CDC) defines TBI as a disruption in the normal function of the brain that can be caused by a bump, blow, or jolt to the head or a penetrating head injury (Marr and Coronado, 2004). Explosive blasts can also cause TBI, particularly among those who serve in the U.S. military. Observing one of the following clinical signs constitutes an alteration in brain function (Menon et al. 2010): (1) Any period of loss of or decreased consciousness; (2) Any loss of memory for events immediately before (retrograde amnesia) or after the injury (post-traumatic amnesia); (3) Neurologic deficits such as muscle weakness, loss of balance and coordination, disruption of vision, change in speech and language, or sensory loss; and (4) Any alteration in mental state at the time of injury such as confusion, disorientation, slowed thinking, or difficulty with concentration.

In the general population, TBI results mainly from falls, motor vehicle/traffic accidents, assaults, and other instances in which the head is struck by or strikes against an object. In the Unites States each year, an estimated 1.7 million people sustain TBI. Of these, 1.365 million are treated and released from an emergency room department, 275,000 are hospitalized, and 52,000 die as a result of their injuries.

TBI is the most common cause of death and disability in persons between 15 and 30 years of age (CDC 2015). In U.S. military service members, TBI may result from the events listed above, or from improvised explosive devices, mortars, grenades, bullets or mines. The Department of Defense (DOD) reports that in 2017 (the most recent full year data), a total of 17,841 service members sustained TBI (Defense and Veterans Brain Injury Center).

Sixty-nine million (95% CI 64-74 million) individuals worldwide are estimated to sustain a TBI each year from all causes (Dewan et al. 2018).

TBI is not a specific diagnosis; the term encompasses a range of conditions. A TBI may be classified as focal or diffuse; open or closed; and mild, moderate, or severe. If the injury is localized to a small area of the brain, it is a focal injury; an injury occurring over a large is diffuse. If the head hits, or is hit by, an object that penetrates the skull and the brain's protective coverings, the injury is open (also called penetrating); otherwise, the injury is closed and can be classified as mild, moderate, or severe 2013).

Currently, no approved drug therapy exists to treat these disorders of consciousness, however off-label use of dopaminergic agents such as amantadine hydrochloride has shown positive responses in Vegetative state (VS) and Minimal conscious state (MCS) patients. Thus, there is a current unmet clinical need for an approved therapy which directly treats moderate to severe TBI patients, allowing them to recover from associated disorders of consciousness in less time.

The present invention incorporates by reference US20200315991A1, which is the applicants' own invention and filing. This prior application describes a method of treating mild and severe traumatic brain injury (TBI) with an intravenous solution of amantadine hydrochloride.

SUMMARY

The present invention provides a regime for use in treating patients with TBI, wherein the amantadine hydrochloride solution is administered intravenously at least twice a day, such that at any time during the wakeful hours of the patient, the plasma levels of amantadine hydrochloride are at no less than 60% of the plasma concentration at the end of the first dose.

In another embodiment, the present invention provides a method of treating TBI with an intravenous composition of amantadine hydrochloride wherein the amount of amantadine hydrochloride administered per day is about 200 mg to about 400 mg, as a single or divided dose.

In another embodiment, the present invention provides a method of treating TBI with an intravenous composition of amantadine hydrochloride wherein the composition is administered twice a day, such that each dose contains about 100 mg of amantadine hydrochloride.

In another embodiment, the present invention provides a method of treating TBI with an intravenous composition of amantadine hydrochloride wherein the composition is administered twice a day, such that each dose contains about 150 mg of amantadine hydrochloride.

In another embodiment, the present invention provides a method of treating TBI with an intravenous composition of amantadine hydrochloride wherein the composition is administered twice a day, such that each dose contains about 200 mg of amantadine hydrochloride.

In another embodiment, the present invention provides a method of treating TBI with an intravenous composition of amantadine hydrochloride wherein the timing of the dose(s) is adjusted in a manner such that a defined sleep cycle is created and maintained in the patient with TBI. More particularly, the total daily dose of the composition is administered during the wakeful hours to the patient.

In one embodiment, the present invention provides a method of treating TBI with an intravenous composition of amantadine hydrochloride wherein the composition is administered twice a day to a patient having TBI such that the first dose and the second dose are separated by a space of about 4 hours to about 6 hours.

In one embodiment, the present invention provides a method of treating TBI with an intravenous composition of amantadine hydrochloride wherein the composition is administered twice a day to a patient having TBI such that at any time during the wakeful hours of the patient, the plasma levels of amantadine hydrochloride are at no less than 60% of the plasma concentration at the end of the first dose.

In another embodiment, the present invention provides a method of treating TBI with an intravenous composition of amantadine hydrochloride wherein the composition is administered twice a day and each dose is administered over a period of about 3 hours.

In yet another embodiment, the present invention provides a method of treating TBI with an intravenous composition of amantadine hydrochloride wherein the composition is administered as two doses that are separated by a period of about 4 hours to about 6 hours, and wherein the second dose of amantadine hydrochloride is completed during the patient's wakeful hours, thereby ensuring that the patient is able to fall asleep and continues to have a defined sleep-wake cycle.

In yet another embodiment, the present invention provides a method of treating TBI with an intravenous composition of amantadine hydrochloride wherein the composition is administered twice a day and each dose is administered at the rate of about 25 mg to about 75 mg of amantadine hydrochloride per hour. In preferred embodiments, the rate of administration is in the range of about 30 mg/hr to about 70 mg/hr of amantadine hydrochloride.

In another aspect, the present invention provides a kit useful for the treatment of TBI, comprising a therapeutically effective amount of a pharmaceutical composition and further comprising instructions for intravenous administration, wherein the intravenous administration rate is greater than or equal to 1 ml/min. In one embodiment, the kit is adapted to be associated with a treatment regimen.

DESCRIPTION

It is important to understand the issues that need to be addressed in patients with TBI. A major concern associated with intracranial injuries in TBI is the management of intracranial pressure (ICP), a resulting factor of TBI which facilitates into intracranial hematoma and/or cerebral edema. These conditions have adverse impact on the brain, and the immediate management and relief of ICP is crucial to the survival and optimal recovery of the patients. Given this serious situation, the fluid content in the body needs to be controlled to prevent further fluid accumulation and rise in ICP. All medications and nutrition are given to the patient by intravenous route, and it is critical to therefore control the volume of fluid being administered, as well as the rate at which the fluids are administered.

Further, sleep-wake disturbances are among the most prevalent and persistent sequelae of TBI. Patients suffering from TBI of any severity, in both the acute and chronic phases, commonly report excessive daytime sleepiness, increased sleep need, insomnia, and sleep fragmentation. Identification and treatment of sleep disorders in patients with TBI is important and can complement other efforts to promote maximum functional recovery. Sleep-wake complaints are reported by approximately one-third of patients within the first 10 days after mild TBI and up to 50 percent at six weeks post-injury. The prevalence is even higher among individuals with severe TBI. There is preliminary evidence that disorders of sleep-wake timing (circadian rhythm sleep-wake disorders), including delayed sleep-wake phase disorder, irregular sleep-wake rhythm disorder, and non-24-hour sleep-wake rhythm disorder, occur with increased frequency in patients with TBI. This can impact the recovery, and the time to optimum recovery of the patient. Therefore, an important aspect in treating patients with TBI is to ensure that a sleep-wake cycle is defined and set, such that the wakeful hours of the patient are similar to normal people, for example the wakeful hours may be from 6 am to 8 pm, or the like.

Aminoadamantane derivatives are weak antagonists of the N-methyl-D-aspartate (NMDA) receptors with neuro-protective properties, and are known to increase dopamine release and block dopamine reuptake (Kornhuber et al., J Neural Transm Suppl., 43:91-104 (1994); Peeters et al., Brain Res., 949:32-41 (2002); and Rogawski et al., CNS Drug Rev., 9(3):275-308 (2003)). Aminoadamantanes also bind to and act as agonists of the alpha-1 receptors (Peeters et al., Eur J Neurosci., 19(8):2212-2220 (2004)). Amantadine hydrochloride, an aminoadamantane derivative, is one of the most commonly prescribed medications for patients with disorders of consciousness who are under-going inpatient neurorehabilitation. While amantadine hydrochloride has been approved for the treatment of parkinsonism and drug-induced extrapyramidal reactions, the tablet, capsule and syrup are administered orally to human subjects, and amantadine hydrochloride has not been approved for use in treating TBI.

Adverse events most commonly (5-10%) associated with use of amantadine hydrochloride include nausea, dizziness, and insomnia. Other known adverse events that are reported less frequently (1-5%) include depression, anxiety and irritability, hallucinations, confusion, anorexia, dry mouth, constipation, ataxia, livedo, reticularis, peripheral edema, orthostatic hypotension, headache, somnolence, nervousness, and fatigue.

Our co-pending application, published as US 20200315991A1 (the '991 application), claims a method of treating traumatic brain injury (TBI) in a human subject comprising parenterally administering a composition comprising a pharmacologically effective amount of amantadine or a pharmaceutically acceptable salt thereof in a pharmaceutically acceptable vehicle, wherein the composition is free of any other excipients. This pending application, while novel in terms of disclosing use of intravenous amantadine hydrochloride in treatment of TBI, broadly discloses that the amantadine hydrochloride may be dosed at 50 mg to 500 mg, once or twice daily, at the rate of about 10 mg/hr to about 150 mg/hr of amantadine hydrochloride, and wherein the composition may have a volume ranging between 50 to 1000 ml, does not teach nor suggest an effective dosing regime that would ensure treatment of the patients with TBI, without impacting recovery.

Given the above understanding about TBI and amantadine hydrochloride, it is extremely important to administer the amantadine hydrochloride in an amount of fluid as low as possible, and at a rate that does not lead to adverse effects, such as increase in ICP. Yet, it is also important to provide the amantadine hydrochloride at a time of the day and at a frequency that ensures a normal sleep-wake cycle for the patient, thereby ensuring sufficient rest at night and preventing unnecessary excitation during the wakeful hours. The '991 application fails to specifically teach the dose of amantadine hydrochloride, the volume in which that dose must be given, as well as the rate at which the dose must be administered. It does not say anything about the timing of the dose(s), except for broadly saying that the dose may be given as a single or divided dose, and divided doses must be spaced apart by 1 to 5 hours.

As discussed above, the volume of fluid is not only critical in terms of increase in ICP, but it is also critical in terms of defining the time of administration of the dose, and therefore, the rate of administration of the dose. The applicants have now found that about 100 mg to about 200 mg of amantadine hydrochloride given in a volume of 250 ml as a single dose is safe, and provides the required efficacy when given twice a day. Each dose is administered over a period of 180 minutes, i.e. at a rate of about 1.39 ml/min. Similarly, the applicants found that administration of amantadine hydrochloride at a rate ranging between 0.5 mg/min to about 1.2 mg/min is safe and efficacious.

A single ascending dose study carried out with 50 mg IV, 100 mg IV, 150 mg IV, 200 mg IV of amantadine hydrochloride was used to understand the rate at which the amantadine hydrochloride is available in the plasma (see Example 1). The study indicated that intravenous amantadine hydrochloride reached a maximum plasma concentration (Tmax) of about 3 to 4 hours and a half-life (T½) of about 11 to about 15 hours. Together with this study, another study conducted to understand the pharmacokinetics of amantadine hydrochloride in the human plasma indicated that at the end of about 4 hours to about 6 hours from the end of the first dose, the level of amantadine hydrochloride in the plasma reduces to about 20% to about 40% of the plasma concentration at the end of the first dose.

It was observed that effective treatment of patients with TBI is achieved by administering two doses of amantadine hydrochloride, wherein the first dose is given in the early hours of morning and the second dose is given such that at any time during the wakeful hours of the patient, the plasma levels of amantadine hydrochloride are at no less than 60% of the plasma concentration at the end of the first dose. The applicants have now found that an effective method of treating patients with TBI is by administering two doses of about 100 mg/250 ml to about 200 mg/250 ml each of amantadine hydrochloride twice daily, wherein the first dose is administered in the early hours of morning, and the second dose is administered after about 4 hours to about 6 hours after the end of the first dose. For example, if the first dose is administered at about 6 am in the morning, the second dose is administered at about 3 pm in the afternoon. As discussed above, each dose is administered over a period of about 180 minutes, i.e. about 3 hours. The advantage with this regime is that an effective dose of amantadine hydrochloride is available to the patient in the wakeful hours, because the early morning dose and the second dose about 4 to about 6 hours thereafter, help in keeping the patient awake, and also work on treating the TBI. Further, because the second dose is given in the afternoon and is completed by early evening, the plasma levels of amantadine hydrochloride fall to levels that are sufficiently low in the evening to ensure that the patient falls asleep. This helps set a sleep-wake cycle that goes a long way in supporting optimum recovery of the patient. The applicants believe that presence of the efficacious plasma levels of amantadine hydrochloride during the wakeful hours of the patient ensures maximum impact in improving consciousness along with maintaining regular sleep-wake cycle.

The present invention provides a method of treating a patient with TBI using intravenous administration of a pharmaceutical composition consisting of a therapeutically effective amount of amantadine hydrochloride and water for injection, wherein the amantadine hydrochloride is administered at a rate of about 0.55 mg/min. The present invention also provides a method of treating a patient with TBI using intravenous administration of a pharmaceutical composition consisting of a therapeutically effective amount of amantadine hydrochloride and water for injection, wherein the amantadine hydrochloride is administered at a rate of about 0.83 mg/min. The present invention provides yet another method of treating a patient with TBI using intravenous administration of a pharmaceutical composition consisting of a therapeutically effective amount of amantadine hydrochloride and water for injection, wherein the amantadine hydrochloride is administered at a rate of about 1.11 mg/min.

The present invention provides a method of treating a patient with TBI using intravenous administration of a pharmaceutical composition consisting of a therapeutically effective amount of amantadine hydrochloride and water for injection, wherein the composition is administered at a rate of 1.4 ml/min.

The present invention also provides a regime for treating a patient with TBI using intravenous administration of a pharmaceutical composition consisting of 100 mg of amantadine hydrochloride in 250 ml of water for injection, wherein the regime includes administration of a first dose of amantadine hydrochloride in the early hours of morning and a second dose at a time when the plasma concentration of amantadine hydrochloride is no less than 60% of the concentration at the end of the first dose, wherein each dose is administered over a period of 180 minutes.

The present invention also provides a regime for treating a patient with TBI using intravenous administration of a pharmaceutical composition consisting of 150 mg of amantadine hydrochloride in 250 ml of water for injection, wherein the regime includes administration of a first dose of amantadine hydrochloride in the early hours of morning and a second dose at a time when the plasma concentration of amantadine hydrochloride is no less than 60% of the concentration at the end of the first dose, wherein each dose is administered over a period of 180 minutes.

The present invention also provides a regime for treating a patient with TBI using intravenous administration of a pharmaceutical composition consisting of 200 mg of amantadine hydrochloride in 250 ml of water for injection, wherein the regime includes administration of a first dose of amantadine hydrochloride in the early hours of morning and a second dose at a time when the plasma concentration of amantadine hydrochloride is no less than 60% of the concentration at the end of the first dose, wherein each dose is administered over a period of 180 minutes.

As described herein, the first and second doses of amantadine hydrochloride are separated by a period of about 4 hours to about 6 hours. It is to be understood that the second dose is administered about 4 hours to about 6 hours after the end of the first dose of amantadine hydrochloride. In preferred embodiments the doses are separated by about 6 hours. In highly preferred embodiments the doses are separated by about 5 hours.

The present invention further provides a regime for treating a patient with TBI using intravenous administration of a pharmaceutical composition consisting of 100 mg of amantadine hydrochloride in 250 ml of water for injection, wherein the regime includes administration of a first dose of amantadine hydrochloride in the early hours of morning and a second dose after about 4 hours to about 6 hours, wherein each dose of 100 mg/250 ml is administered over a period of 180 minutes.

The present invention further provides a regime for treating a patient with TBI using intravenous administration of a pharmaceutical composition consisting of 150 mg of amantadine hydrochloride in 250 ml of water for injection, wherein the regime includes administration of a first dose of amantadine hydrochloride in the early hours of morning and a second dose after about 4 hours to about 6 hours, wherein each dose of 150 mg/250 ml is administered over a period of 180 minutes.

The present invention further provides a regime for treating a patient with TBI using intravenous administration of a pharmaceutical composition consisting of 200 mg of amantadine hydrochloride in 250 ml of water for injection, wherein the regime includes administration of a first dose of amantadine hydrochloride in the early hours of morning and a second dose after about 4 hours to about 6 hours, wherein each dose of 200 mg/250 ml is administered over a period of 180 minutes.

The amantadine hydrochloride solution used in the regime of the present invention is a sterile aqueous solution of amantadine hydrochloride in water for injection, and is described in the applicants' co-pending application, i.e. the '991 publication. The process used for the preparation of the same is described in the '991 publication and is incorporated herein by reference.

Any numerical value described herein that is preceded by the term "about" means that the numerical value covers a range of ±10% of the stated value.

Example 1

An open-label, multiple-cohort, single-period non-randomized single-ascending dose fasted study was carried out to evaluate safety, tolerability, and pharmacokinetics of amantadine hydrochloride IV solution, 50 mg/ml in healthy adult subjects. The primary objective of this study was to assess the safety and tolerability of single ascending doses of amantadine hydrochloride IV solution, 50 mg/mL over the dose range of 100 mg to 200 mg when infused over a 180-minute period in healthy adult subjects. The secondary objective was to evaluate the pharmacokinetics of single ascending doses of amantadine hydrochloride IV solution, 50 mg/mL over the dose range of 100 mg to 200 mg when infused over a 180-minute period in healthy adult male and female subjects. Thus, this open-label, single-ascending dose, multiple-cohort, single-period study was conducted with 24 healthy, non-tobacco-, non-nicotine-using, adult male and female subjects (8 subjects per cohort) to evaluate the safety, tolerability, and pharmacokinetics of amantadine hydrochloride IV solution, 50 mg/mL when infused over a 180-minute period over the dose range of 100 mg, 150 mg and 200 mg. The subjects received the test treatments as described in Table 1 below, under direct observation following an overnight fast of at least 10 hours.

TABLE 1

Treatments administered

Cohort 1: Treatment A (100 mg dose) - Amantadine Hydrochloride IV Solution, 50 mg/mL; 2 mL of solution, diluted into 280 mL* of sterile IV saline solution, infused over a 180-minute period [100 mg total dose]
Cohort 2: Treatment B (150 mg dose) - Amantadine Hydrochloride IV Solution, 50 mg/mL; 3 mL of solution, diluted into 280 mL* of sterile IV saline solution, infused over a 180-minute period [150 mg total dose]
Cohort 3: Treatment C (200 mg dose) - Amantadine Hydrochloride IV Solution, 50 mg/mL; 4 mL of solution, diluted into 280 mL* of sterile IV saline solution, infused over a 180-minute period [200 mg total dose]

*The initial amount of 280 mL was determined based on the fill volume data provided by Baxter regarding the 250 mL VIAFLEX bags.

Plasma concentrations of amantadine increased rapidly and reached maximum plasma concentrations at around 3 hours after start of the IV infusion. Thereafter, plasma levels declined monophasically, with mean elimination half-life of approximately 11.5 to 14.5 hours, and remained detectable for more than 48 to 72 hours post-dose.

Pharmacokinetic parameters of amantadine assessed after administration of amantadine hydrochloride IV solution at dose levels of 100, 150 and 200 mg infused over 180 minutes are presented in Table 2 below. Following the 100 mg and 200 mg doses, the $C_{max}$ and $AUC_{0-\infty}$ values increased more than proportionally to the dose, by almost 2.3-fold for $C_{max}$ and 3-fold for $AUC_{0-28}$.

TABLE 2

| Dose (mg) | Cmax (ng/ml) | $AUC_{0-\infty}$ (h · ng/ml) | AUC0-24 (h · ng/ml) | Tmax (hr) | T1/2 (hr) |
|---|---|---|---|---|---|
| 100 | 278.67 | 4397.04 | 3316.31 | 3 | 11.41 |
| 150 | 523.46 | 6850.07 | 5587.71 | 3 | 11.55 |
| 200 | 643.31 | 13166.30 | 9784.83 | 3.25 | 14.51 |

Example 2

A study was conducted with 14 healthy, non-tobacco, non-nicotine-using, adult male and female subjects to monitor the safety and tolerability of amantadine hydrochloride IV solution, 50 mg/mL (4 mL×50 mg/mL, 200 mg total dose). 4 mL venous blood was collected before dosing (0 hour) and at the following nominal times after dosing: 0.5, 1, 2, 3, 4, 5, 5.5, 6, 7, 9, 12, 16, 24, 36, 48 and 72 hours post-dose. Safety was assessed by qualified study staff by evaluating the following: reported adverse events, clinical laboratory test results, vital sign measurements, ECG findings, physical examination findings at screening and clinic exit (including body weight and height measurements), and concomitant medication usage. The blood samples collected were used to assess the decrease in concentration of amantadine in the plasma over time, and is tabulated in Table 3 below.

TABLE 3

| Time (hr) after First Dose | % decrease in plasma amantadine concentration |
|---|---|
| 0 | 0.0 |
| 1 | 14.0 |
| 2 | 20.9 |
| 2.5 | 24.5 |
| 3 | 26.2 |
| 4 | 30.0 |
| 6 | 34.5 |
| 9 | 48.3 |

Example 3

The plasma amantadine concentrations from healthy adults enrolled in the open-label, multiple-cohort, single-period non-randomized single-ascending dose study of Example 1 were used to determine the decrease in concentration of amantadine over time, after the administration of the first dose of 100 mg and 150 mg in different cohorts. The decrease in concentration over time is tabulated in Table 4 below. The data is supportive in determining the timing of the second dose of amantadine.

TABLE 4

| Time (hr) after First Dose | % decrease in plasma amantadine concentration | |
|---|---|---|
| | 100 mg | 150 mg |
| 0 | 0.0 | 0.0 |
| 0.5 | 12.9 | 15.3 |
| 1 | 16.2 | 17.9 |
| 1.5 | 18.6 | 21.3 |
| 2 | 23.0 | 25.3 |
| 2.5 | 27.1 | 30.3 |
| 3 | 28.8 | 32.8 |
| 4 | 31.7 | 35.3 |
| 5 | 34.7 | 37.9 |

TABLE 4-continued

| Time (hr) after First Dose | % decrease in plasma amantadine concentration | |
|---|---|---|
| | 100 mg | 150 mg |
| 7 | 41.0 | 44.4 |
| 9 | 49.3 | 52.7 |

We claim:

1. A dosing regimen for administering a liquid pharmaceutical composition of amantadine hydrochloride to a patient having a traumatic brain injury, the regimen comprising:
   administering a first dose of the liquid pharmaceutical composition of amantadine hydrochloride by an intravenous route, wherein the first dose comprises between 100 mg and 200 mg of amantadine hydrochloride in an aqueous solution of about 200 ml to about 300 ml over a period of about two to about four hours to define a completion of administration of the first dose; and
   administering a second dose of the liquid pharmaceutical composition of amantadine hydrochloride by an intravenous route, wherein the second dose comprises between 100 mg and 200 mg of amantadine hydrochloride in an aqueous solution of about 200 ml to about 300 ml over a period of about two to about four hours,
   wherein the second dose is administered after four to six hours after the completion of administration of the first dose and wherein the time for administration of the second dose is selected such that a plasma concentration of amantadine is at least 60% of the plasma concentration of amantadine in the patient immediately after the completion of administration of the first dose.

2. The dosing regimen of claim 1, wherein the first dose, the second dose or both the first and the second dose are administered at a rate of about 25 mg/hour to about 75 mg/hour.

3. The dosing regimen of claim 1, wherein the first dose, the second dose or both the first and the second dose are administered at a rate of about 0.5 mg/min to about 1.2 mg/min.

4. The dosing regimen of claim 1, wherein the first dose, the second dose or both the first and the second dose are administered at a rate of about 1.35 ml/min to about 1.45 ml/min of the solution.

5. The dosing regimen of claim 4, wherein the first dose, the second dose or both the first and the second dose are administered at a rate of about 1.39 ml/min to about 1.41 ml/min of the solution.

6. The dosing regimen of claim 5, wherein the first dose, the second dose or both the first and the second dose are administered at a rate of about 1.40 ml/min of the solution.

7. The dosing regimen of claim 1, wherein the second dose is administered about five hours after the completion of administration of the first dose.

8. The dosing regimen of claim 1, wherein the second dose is administered at about four hours to less than about five hours after the completion of administration of the first dose.

9. The dosing regimen of claim 1, wherein the second dose is administered at five hours to six hours after the completion of administration of the first dose.

10. The dosing regimen of claim 1, wherein the second dose is administered at a time after the completion of administration of the first dose, wherein the time for administration of the second dose is selected such that a plasma concentration of amantadine is between 60% and 80% of the plasma concentration of amantadine in the patient immediately after the completion of administration of the first dose.

11. The dosing regimen of claim 1, wherein the pharmaceutical composition consists essentially of a therapeutically effective amount of amantadine hydrochloride and water for injection in saline.

12. The dosing regimen of claim 1, wherein the pharmaceutical composition consists of a therapeutically effective amount of amantadine hydrochloride and water for injection in saline.

13. The dosing regimen of claim 1, wherein the aqueous solution of the first dose and/or the second dose is about 250 ml.

14. A method of treating a patient having a traumatic brain injury, the method comprising:
    administering a first dose of a liquid pharmaceutical composition of amantadine hydrochloride by an intravenous route, wherein the first dose comprises between 100 mg and 200 mg of amantadine hydrochloride in an aqueous solution of about 250 ml over a period of about three hours to define a completion of administration of the first dose; and
    administering a second dose of the liquid pharmaceutical composition of amantadine hydrochloride by an intravenous route, wherein the second dose comprises between 100 mg and 200 mg of amantadine hydrochloride in an aqueous solution of about 250 ml over a period of about three hours,
    wherein the second dose is administered after about four to six hours after the completion of administration of the first dose and wherein the time for administration of the second dose is selected such that a plasma concentration of amantadine is at least 60% of the plasma concentration of amantadine in the patient immediately after the completion of administration of the first dose.

15. A dosing regimen for administering a liquid pharmaceutical composition of amantadine hydrochloride to a patient having a traumatic brain injury, the regimen comprising:
    administering a first dose of the liquid pharmaceutical composition of amantadine hydrochloride by an intravenous route, wherein the first dose comprises between 100 mg and 200 mg of amantadine hydrochloride in an aqueous solution over a period of about two to about four hours to define a completion of administration of the first dose; and
    administering a second dose of the liquid pharmaceutical composition of amantadine hydrochloride by an intravenous route, wherein the second dose comprises between 100 mg and 200 mg of amantadine hydrochloride in an aqueous solution over a period of about two to about four hours,
    wherein the second dose is administered at a time after the completion of administration of the first dose, wherein the time for administration of the second dose is selected such that a plasma concentration of amantadine is at least 60% of the plasma concentration of amantadine in the patient immediately after the completion of administration of the first dose.

16. The dosing regimen of claim 15, wherein the second dose is administered after four to six hours after the completion of administration of the first dose.

17. The dosing regimen of claim 15, wherein the second dose is administered about five hours after the completion of administration of the first dose.

18. The dosing regimen of claim 17, wherein the second dose is administered at about four hours to less than about five hours after the completion of administration of the first dose.

19. The dosing regimen of claim 15, wherein the aqueous solution of the first dose and/or the second dose is about 250 ml.

20. A dosing regimen for administering a liquid pharmaceutical composition of amantadine hydrochloride to a patient having a traumatic brain injury, the regimen comprising:
  administering a first dose of the liquid pharmaceutical composition of amantadine hydrochloride by an intravenous route, wherein the first dose comprises between 100 mg and 200 mg of amantadine hydrochloride in an aqueous solution of about 200 ml to about 300 ml over a period of about two to about four hours to define a completion of administration of the first dose; and
  administering a second dose of the liquid pharmaceutical composition of amantadine hydrochloride by an intravenous route, wherein the second dose comprises between 100 mg and 200 mg of amantadine hydrochloride in an aqueous solution of about 200 ml to about 300 ml over a period of about two to about four hours, wherein the second dose is administered after four to six hours after the completion of administration of the first dose and wherein the first dose and the second dose are administered at a rate of about 25-75 mg/hour.

21. A dosing regimen for administering a liquid pharmaceutical composition of amantadine hydrochloride to a patient having a traumatic brain injury, the regimen comprising:
  administering a first dose of the liquid pharmaceutical composition of amantadine hydrochloride by an intravenous route, wherein the first dose comprises between 100 mg and 200 mg of amantadine hydrochloride in an aqueous solution of about 200 ml to about 300 ml over a period of about two to about four hours to define a completion of administration of the first dose; and
  administering a second dose of the liquid pharmaceutical composition of amantadine hydrochloride by an intravenous route, wherein the second dose comprises between 100 mg and 200 mg of amantadine hydrochloride in an aqueous solution of about 200 ml to about 300 ml over a period of about two to about four hours, wherein the second dose is administered after four to six hours after the completion of administration of the first dose and wherein the first dose and the second dose are administered at a rate of about 1.35-1.45 ml/min.

* * * * *